United States Patent [19]

Mitchell

[11] 4,141,969
[45] Feb. 27, 1979

[54] DENTIFRICES CONTAINING AMORPHOUS SILICA

[75] Inventor: Robert L. Mitchell, Somerset, N.J.

[73] Assignee: Colgate-Palmolive Company, New York, N.Y.

[21] Appl. No.: 770,344

[22] Filed: Feb. 22, 1977

[51] Int. Cl.$^2$ .......................... A61K 7/18; B65D 85/14; B65D 81/24; B65D 81/26

[52] U.S. Cl. .................................. 424/52; 206/277; 206/524.4

[58] Field of Search ..................... 424/49–58; 206/277, 524.4

[56] References Cited

U.S. PATENT DOCUMENTS

| | | | |
|---|---|---|---|
| 1,817,664 | 8/1931 | Badanes | 424/49 |
| 3,662,060 | 5/1972 | Clippingdale et al. | 424/57 |
| 3,678,155 | 7/1972 | Clippingdale et al. | 424/52 |
| 3,842,168 | 10/1974 | Colodney | 424/52 |
| 3,864,470 | 2/1975 | Watson | 424/49 |
| 3,906,090 | 9/1975 | Colodney | 424/52 |
| 3,911,102 | 10/1975 | Harrison | 424/49 |
| 3,911,104 | 10/1975 | Harrison | 424/52 |
| 3,937,804 | 2/1976 | Delaney et al. | 424/49 |
| 3,939,262 | 2/1976 | Kim | 424/52 |
| 3,991,177 | 11/1976 | Vidra et al. | 424/50 |
| 4,024,239 | 5/1977 | Pader | 424/57 |
| 4,038,380 | 7/1977 | Cordon | 424/49 |
| 4,058,595 | 11/1977 | Colodney | 424/50 |

FOREIGN PATENT DOCUMENTS 1559196 3/1969 France.
1188353 4/1970 United Kingdom ...................... 424/52

OTHER PUBLICATIONS

Chem. Abstracts 72 #15769t (1970) of Unilever Fr. 1,559,196 Mar. 7, 1969, "Toothpaste Containing A-Alumina Trihydrate and PPTD.SiO$_2$".

Primary Examiner—Shep K. Rose
Attorney, Agent, or Firm—Robert L. Stone; Murray M. Grill; Herbert S. Sylvester

[57] ABSTRACT

Dentifrice containing a compound which provides fluorine, amorphous silica polishing agent and an additive which supplies calcium ions. The dentifrice is compatible with an unlined aluminum container.

11 Claims, No Drawings

DENTIFRICES CONTAINING AMORPHOUS SILICA

This invention relates to a dentifrice containing an amorphous silica polishing agent. Amorphous silica polishing agents for dentifrices which are synthetic, precipitated materials and include amounts of combined alumina have been described in U.S. Pat. Nos. 3,911,102, 3,911,104 and 3,906,090, as well as in aspects of U.S. Pat. Nos. 3,893,848 and 3,928,541. Further amorphous precipitated silica polishing agents have been developed with are substantially free of alumina, except for that which may be present as an impurity. Such polishing agents have been described in further aspects of U.S. Pat. Nos. 3,893,840 and 3,928,541 as well as in U.S. Pat. No. 3,960,586.

These agents which are substantially free of alumina have been found to have desirable polishing properties. However, when employed in toothpastes which include a compound which provides fluorine such as sodium fluoride or sodium monofluorophosphate they generally are incompatible with the unlined surface of an aluminum dentifrice container; in particular causing the swelling and formation of gas on the tube wall and also corroding the wall itself. Occasional lots of the amorphous silica are compatible with the aluminum surface. However, it is difficult to reproduce such lots.

It is an advantage of this invention that an additive is provided which renders amorphous silica polishing agent in the presence of a compound which provides fluorine compatible with the surface of an unlined aluminum container. Other advantages will be apparent from consideration of the following disclosure.

In accordance with certain of its aspects this invention relates to a dental cream composition comprising a dental vehicle and dispersed therein synthetic precipitated silica essentially free of alumina which silica has an aggregate particle size of about 2 to 20 microns and an essentially amorphous X-ray structure, a compound which provides fluorine in amount about 0.01–1% by weight and a calcium salt in amount to provide at least about 0.01 to about 0.3% by weight of calcium ions in water.

In accordance with preferred aspects of the invention, the stability of the dental cream is enhanced by the presence of hydrated alumina, preferably alpha-alumina trihydrate in minor amount, such as about 0.25–10% by weight.

In accordance with further aspects of this invention, the dental cream is packaged in an unlined aluminum container or dental cream tube, with which it remains compatible upon aging.

The precipitated amorphous silica dental polishing agent is present in amount of about 5–50% by weight, preferably about 10–35%. The silica is essentially free of alumina (beyond that inherently present as impurity) and is typified by the description of such materials in U.S. Pat. Nos. 3,893,840, 3,928,541 and 3,960,586, the disclosures of which are incorporated herein by reference. Thus it can have a wet cake moisture content of less than about 75%, such as between about 50 and 70% (a low wet cake content); an oil absorption of less than about 125 cc/100 gm., e.g., less than about 110cc/100gm; a pack density of more than about 12 pounds/cubic foot; and a valley abrasion of more than about 5.0 mg. wire loss, e.g., about 10mg to 168 mg. The surface area is typically less than about 120 $m^2$/gm, preferably about 30 $m^2$/gm.–100 $m^2$/gm.

The compound which contains and provides fluorine has a beneficial effect on the care and hygiene of the oral cavity, e.g., diminution of enamel solubility in acid and protection of the teeth against decay. Examples thereof include sodium fluoride, stannous fluoride, potassium fluoride, potassium stannous fluoride, ($SnF_2KF$), sodium hexafluorostannate, stannous chlorofluoride, sodium fluorzirconate and sodium monofluorophosphate. These materials, which dissociate or release fluorine containing ions in water are present in an effective but non-toxic amount providing about 0.01–1% by weight of fluorine. Sodium fluoride (about 0.02–2%) and sodium monofluorophosphate (about 0.075–7.6%) are preferred.

The calcium salt additive which stabilizes the dental cream of the invention in an unlined aluminum container may be a water-soluble or a substantially water-insoluble compound. Since the compound should be ionizable in water to provide at least about 0.01% to about 0.3% of calcium ions, the water-soluble compounds such as the chloride, bromide, iodide, acetate and nitrate salts of calcium are preferred particularly since greater amounts of substantially water-insoluble salts, such as the carbonate, metasilicate and phosphate of calcium, would be necessary. It is noted that the phosphate moiety of dicalcium phosphate may exert a stabilizing effect independent of the calcium ions, even when less than about 0.01% of calcium ions would ionize. The most preferred calcium salts are the soluble halides (chloride, bromide and iodide) and especially the chloride.

The amount of calcium provided by the calcium salt should be at least about 0.01% to about 0.3% or somewhat more, based upon the water-solubility of the salt. When the amount of the salt is such that less than about 0.01% calcium ion is solubilized in water (e.g., 0.02% calcium chloride - anhydrous provides about 0.007% calcium ions), the dental cream would cause formation of gas pockets on an aluminum container surface (air on wall) and substantial etching and swelling of the container. When the amount of the salt is such that about 0.01–0.02% calcium ion is solubilized in water (e.g., corresponding to about 0.03–5% calcium chloride-anhydrous) optimum container compatibility can be achieved. When the amount of calcium ion provided in water is greater than about 0.02% the dental cream thickens somewhat, but substantial compatibility is achieved. This is so even when the amount of calcium ion is about 0.3% (e.g., with about 0.7% calcium chloride. At substantially higher amounts of calcium, such as about 0.72% (corresponding to about 2% calcium chloride) compatibility with an aluminum container is substantially lost.

If desired the dental cream may contain a metallic salt additive to provide metal ions in addition to the calcium ions. Magnesium salts and particularly water-soluble magnesium salts such as magnesium chloride can be particularly desirable. Typical amounts of such additional metal ion are at least about 0.01% by weight, preferably about 0.01–0.3%.

A minor amount, e.g., at least about 0.25% of a hydrated alumina, such as alpha-alumina trihydrate, may be added to the dental cream. The hydrated alumina assists in polishing and reduces the tendency of the dental cream to separate into the compatibility of the composition with an unlined aluminum tube. The hydrated alumina can comprise about 10% by weight of the dental cream. About 1-2% by weight is preferred. The polishing ability of the dental cream may also be supplemented with a minor amount, e.g., about 0.5-5% by weight, preferably about 0.5-1%, of a hard abrasive, such as calcined alumina or zirconium silicate.

In the dental cream formulation, the liquids and solids are necessarily proportioned to form a cream mass of desired consistency which is extrudible from a collapsible unlined aluminum container. In general, the liquids in the dental cream will comprise chiefly water, glycerine, aqueous solutions of sorbitol, propylene glycol, polyethylene glycol 400, etc., including suitable mixtures thereof. It is advantageous usually to use a mixture of both water and a humectant or binder such as glycerine or sorbitol. The total liquid content will generally be about 20-75% by weight of the formulation. It is preferred to use also a gelling agent in dental creams such as the natural and synthetic gums and gumlike materials, e.g., Irish moss, gum tragacanth, methyl cellulose hydroxyethyl cellulose, sodium carboxymethyl cellulose, polyvinylpyrrolidone, and starch, usually in an amount up to about 10%, and preferably about 0.2-5% of the formulation. The preferred gelling agents are methyl cellulose and hydroxyethyl cellulose.

Organic surface-active agents used in the compositions of the present invention to achieve increased prophylactic action, assist in achieving thorough and complete dispersion of the instant compositions throughout the oral cavity, and render the instant compositions more cosmetically acceptable. The organic surface-active material may be anionic, nonionic, ampholytic, or cationic in nature, and it is preferred to employ as the surface-active agent a detersive material which imparts to the composition detersive and foaming properties. Suitable such detergents are water-soluble salts of higher fatty acid monoglyceride monoglyceride monosulfates, such as sodium lauryl sulfate, alkyl aryl sulfonates, such as sodium dodecyl benzene sulfonate, higher alkyl sulfoacetates, higher fatty acid ester of 1,2 dihydroxy propane sulfonates, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium and ethanolamine salts of N-lauroyl, N-myristoyl or N-palmitoyl sarcosine which should be substantially free from soap or similar higher fatty acid material which tends to substantially reduce the effect of these compounds. The use of these sarcosinate compounds in dentifrice compositions of the present invention is particularly advantageous since these materials exhibit a prolonged and marked effect in the inhibition of acid formation in the oral cavity due to carbohydrates breakdown in addition to exerting some reduction in the solubility of tooth enamel in acid solutions.

Other particularly suitable surface-active materials include nonionic agents such as condensates of sorbitan monostearate with approximately 60 moles of ethylene oxide, consensates of ethylene oxide with propylene oxide condensates of propylene glycol (available under the trademark ("Pluronics") and amphoteric agents such as quaternized imidazole derivatives which are available under the trademark "Miranol" such as Miranol C₂M. Cationic surface-active germicides and antibacterial compounds such as diisobutylphenoxyethoxyethyl dimethyl benzyl ammonium chloride, benzyl dimethyl stearyl ammonium chloride, tertiary amines having one fatty alkyl group (of from 12 to 18 carbon atoms) and two (poly) oxyethylene groups attached to the nitrogen (typically containing a total of from about 2 to 50 ethanoxy groups per molecule) and salts thereof with acids and compounds of the structure

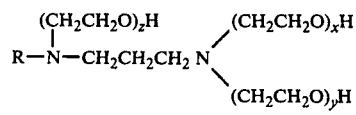

where R is a fatty alkyl group containing from about 12 to 18 carbon atoms, and x, y, and z total 3 or higher, as well as salts thereof with mineral or organic acids, may also be used. It is preferred to use from about 0.05 to 5% by weight of the foregoing surface-active materials in the instant oral preparations.

Various other materials may be incorporated in the oral preparations of this invention. Examples thereof are coloring or whitening agents, preservatives, silicones, chlorophyll compounds, ammoniated materials such as urea, diammoniumphosphate and mixtures thereof, and other constituents. These adjuvants are incorporated in the instant compositions in amounts which do not substantially adversely affect the properties and characteristics desired and are selected and used in proper amount depending upon the particular type of preparation involved.

The dental cream typically has a pH (determined directly on the cream) of about 4.5 to 10, preferably about 5-9. If desired, the pH may be adjusted with an acidic material, such as benzoic or citric acid, or an alkaline material, such as sodium hydroxide, to achieve a particular value. Buffering agents, e.g., phosphate buffers, may be used.

The dental cream may be prepared by conventional means with the calcium (and if present, other metal salt) being added to the cream gel vehicle. The gel is formed by dispersing a gelling agent with a preservative (e.g., sodium benzoate) and humectant water may be present too. Polishing material, surface-active agent, the additive providing calcium ion and flavor are then added.

The following specific examples are further illustrative of the nature of the present invention but is is understood that the invention is not limited thereto. The composition are prepared in the usual manner and all amounts and proportions are by weight unless otherwise specified.

EXAMPLE 1

The following dental cream is prepared and placed in an lined aluminum toothpaste tube and aged at 43° C. and 49° C.

| Ingredients | Parts |
|---|---|
| Glycerine | 25 |
| Sodium benzoate | 0.5 |
| Sodium saccharin | 0.2 |
| Sodium carboxymethyl cellulose | 1.1 |
| Sodium monofluorophosphate | 0.76 |
| Amorphous silica | 30 |
| Calcined alumina | 0.5 |
| Alpha alumina trihydrate | 1.0 |
| Titanium dioxide | 0.5 |
| Sodium lauryl sulfate | 1.5 |
| Flavor | 1 |
| Water | Q.S. to 100 |

The amorphous silica is a synthetic product substantially free of alumina (Al content being only 0.20%) in accordance with U.S Pat. No. 3,893,840; for instance having an oil absorption of 108 cc/100 gm and a surface area of 64 m²/gm. Its Si content is 38.2%. Its trace element content is:

|    | %      |
|----|--------|
| Ca | 0.0025 |
| Fe | 0.35   |
| Na | 1.70   |
| Al | 0.20   |
| Mg | 0.008  |

The following observations were made on the dental cream and the tube upon aging for the indicated periods of time at 43° C. and 49° C.:

|          | 49° C                                                                                      | 43° C                                                                       |
|----------|--------------------------------------------------------------------------------------------|-----------------------------------------------------------------------------|
| 3 Weeks  | Severe tube swelling; Air on wall; black stain on tube; tube wall wet; no precipitation or visible etching. | Severe tube swelling; Black tube stain; tube wall wet; no precipitation or visible etching. |
| 6 Weeks  | Tube swelling; black tube stain; tube wall wet; air on wall; no precipitation or visible etching. | Air on wall; black tube stain; severe tube staining; tube wall wet with cream separation. |
| 9 Weeks  | Air on wall; tube swelling; black tube stain; tube wall wet and etched. | Tube swelling; black tube stain; tube wall wet; air on wall. |

This dental cream is not compatible with its aluminum container.

EXAMPLE 2

The dental cream of Example 1 is modified by including therein respectively. 0.02, 0.03, 0.05, 0.06, 0.3 and 0.7 parts of calcium chloride (with 0.7% calcium chloride, 1.0% sodium carboxymethyl cellulose was employed). The following observations are made on aging:

| Parts of $CaCl_2$ | Aging Time | 49° C | 43° C |
|---|---|---|---|
| 0.02 | 3 Weeks | No tube swelling; off smell; trace to slight air on wall; tube wall wet; grey tube stain; etching. | No tube swelling; no off smell; no tube wall wetting; very slight air on wall; grey-gold tube stain. |
|  | 6 Weeks | No tube swelling; off smell; slight air on wall; tube wall wet; grey stain; etching. | No tube swelling; air on wall; no tube swelling; off smell. |
|  | 9 Weeks | Gas pockets wet; air on wall; gold stain, etching. | Air on wall, no tube swelling; gold stain. |
| 0.03 | 3 Weeks | No tube swelling; tube off smell; no air on wall or wall wetting; no apparent breakdown of cream; no etching or precipitation | No tube swelling; trace of gold tube stain; no air on wall; no wall wetting; no arrarent cream breakdown. |
|  | 6 Weeks | Cream O.K.; slight gold tube stain; etching. | Cream O.K.; slight gold stain. |
|  | 9 Weeks | Cream O.K.; gold stain; etching and precipitation in crimp end. | Cream O.K.; gold stain. |
| 0.05 | 3 Weeks | No tube swelling; no tube staining; off smell; trace of tube wall wetting; etching and white precipitate at crimp end. | No tube swelling; no stain; no off smell. |
|  | 6 Weeks | Cream O.K.; gold stain with etching and white precipitate at crimp end. | O.K. |
|  | 9 Weeks | Cream O.K.; etching at crimp end with white precipitate | O.K. |
| 0.06 | 3 Weeks | Trace of cap wetting; trace of wall wetting; off smell; no air on wall; no tube swelling; no tube staining; etching and precipitate at crimp end. | Trace cap wetting; no wall wetting; trace off smell; no air on wall; no tube swelling; no tube staining. |
|  | 6 Weeks | Trace of cap wetting; cream O.K.; white precipitate and etching at crimp end. | Cream O.K.; trace of cap wetting. |
|  | 9 Weeks | Cap wet etching and white deposit in crimp area; cream slightly thick. | Separation at cap; white deposit in crimp end; cream thick. |
| 0.30 | 3 Weeks | Trace of gas pocket wetting; etching and precipitate at crimp end. | O.K. |
|  | 6 Weeks | Cream O.K.; etching precipitate at crimp end. | Cream O.K.; precipitate at crimp end. |
|  | 9 Weeks | Cream O.K.; etching and precipitate at crimp end; cream thick. | Cream O.K.; precipitate at crimp end; cream thick. |
| 0.70 | 3 Weeks | Grit (precipitate) adheres to walls; no visible tube swelling; spongy cream; no tube stain; wall is wet; white precipitate on walls. | White precipitate on walls causing dark brown spots where precipitate contacts walls; wall is wet; spongy cream. |
|  | 6 Weeks | precipitate; no tube swelling; trace blue color on cream (possibly from tube dye); no wall wet; no air on wall. | Wall wet and separation; white precipitate on walls; no air on walls; spongy and thick cream. |
|  | 9 Weeks | No tube swelling; no air on wall; off color; spongy; grit (precipitate). | Precipitate on walls; off white cream; no air on wall; no swelling; spongy. |

In the observations of this Example, the dental cream containing 0.02 parts of calcium chloride (corresponding to about 0.007 parts of $Ca^{+2}$ ion) achieves better compatibility with the aluminum tube than does the dental cream of Example 1. However, the gas and air on wall formation is such that a desirable degree of compatibility is not attained.

The dental creams containing 0.03 and 0.05 parts of calcium chloride (corresponding to about 0.01–0.02 parts of $Ca^{+2}$ ion) achieves optimum compatibility with the aluminum tubes. The etching and precipitation at the crimp are not substantially deleterious. Likewise, the etching and precipitation observed with the creams containing 0.06, 0.3 and 0.7 parts of calcium chloride (corresponding to about 0.022, 0.1 and 0.25 parts of $Ca^{+2}$ ion respectively) are not substantially deleterious. The creams containing these latter amounts of calcium salt tend to be somewhat thicker than when the lower amounts of the calcium salt are employed.

EXAMPLE 3

Desirable aging is achieved for 3, 6 and 9 weeks at 43° C. and 49° C. in aluminum tubes with dental cream of the formula of Example 1 modified by including 0.07 parts of calcium chloride and 0.10 part of magnesium chloride and with 1.0 part of sodium carboxymethyl cellulose, rather than 1.1 parts.

EXAMPLE 4

The following dental creams are tubed in unlined aluminum toothpaste tubes. After aging for 3, 6 and 9 weeks at 43° C. and 49° C. they are observed to be substantially compatible with the tubes.

| Ingredients | Parts by Weight Dental Cream | |
|---|---|---|
| | A | B |
| Glycerine | 25 | 25 |
| Sodium benzoate | 0.5 | 0.5 |
| Sodium saccharine | 0.2 | 0.2 |
| Sodium carboxymethyl cellulose | 1 | 1 |
| Sodium monofluorophosphate | 0.76 | 0.76 |
| Amorphous slica (as in Example 1) | 28 | 28 |
| Calcined alumina | 0.5 | 0.5 |
| Alpha alumina trihydrate | — | 1 |
| Calcium metasilicate | 2 | 2 |
| Titanium dioxide | 0.5 | 0.5 |
| Sodium lauryl sulfate | 1.5 | 1.5 |
| Flavor | 1 | 1 |
| Water | Q.S. to 100 | Q.S. to 100 |

It is understood that a small amount of alumina is generally present as impurity in the synthetic precipitated silica. Such silicas which are "essentially free of alumina" typically contain no more than about 0.4% by weight aluminum, e.g., about 0.4%–0.2% by weight aluminum.

Although this invention has been described with reference to specific examples, it will be apparent to one skilled in the art that various modifications may be made thereto which fall within its scope.

I claim:

1. A dental cream composition compatible with the surface of an unlined aluminum container and contained in said container, comprising a dental vehicle and dispersed therein about 10–35% by weight of a polishing agent consisting essentially of synthetic precipitated silica essentially free of alumina which silica has a wet cake moisture content of less than about 75%, an oil absorption of less than about 125 cc/gm, a pack density of more than about 12 pounds/cubic foot, a valley abrasion of more than about 5.0 mg wire loss, a surface area of less than about 120m$^2$/gm, an aggregate particle size of about 2 to 20 microns and an essentially amorphous x-ray structure, a compound which provides fluorine in amount of about 0.01 to 1% by weight and a water-soluble calcium salt selected from the group consisting of chloride, bromide, iodide, acetate and nitrate in amount to provide at least about 0.01% to about 0.3% by weight of calcium ion in water, said dental cream otherwise being substantially calcium free and causing formation of gas pockets on an aluminum container surface, air on wall and substantially etching and swelling of the container when the amount of the calcium salt is such that less than about 0.01% calcium ion is solubilized in water and compatibility with said aluminum container being substantially lost at substantially higher amount of calcium than about 0.3% by weight of calcium ion in water.

2. The dental cream composition claimed in claim 1 wherein said compound which provides fluorine is selected from the group consisting of sodium fluoride and sodium monofluorophosphate.

3. The dental cream composition claimed in claim 2 wherein said compound which provides fluorine is sodium monofluorophosphate.

4. The dental cream composition claimed in claim 1 wherein said calcium salt is a halide selected from the group consisting of chloride, bromide and iodide salts of calcium.

5. The dental cream composition claimed in claim 4 wherein said calcium salt is calcium chloride.

6. The dental cream composition claimed in claim 1 wherein said calcium salt is in amount to provide about 0.01 to 0.02% calcium ion in water.

7. The dental cream composition claimed in claim 6 wherein said calcium compound is calcium chloride.

8. The dental cream composition claimed in claim 4 wherein a magnesium salt is additionally present in amount to provide at least about 0.01 to 0.3% of magnesium ions in water.

9. The dental cream composition claimed in claim 1 wherein about 0.5 to 5% by weight of a hard abrasive selected from the group consisting of calcined alumina and zirconium silicate is additionally present.

10. The dental cream composition claimed in claim 9 wherein said hard abrasive is calcined alumina.

11. The dental cream composition claimed in claim 1 wherein said composition has a pH of about 4.5 to 10.

* * * * *